US008706201B2

(12) United States Patent
Beker et al.

(10) Patent No.: US 8,706,201 B2
(45) Date of Patent: Apr. 22, 2014

(54) APPARATUS AND METHOD FOR ANALYSIS OF HIGH FREQUENCY QRS COMPLEXES

(75) Inventors: Amir Beker, Rosh HaAyin (IL); Orna Bregman-Amitai, Tel-Aviv (IL); Alexander Zeltser, Natania (IL)

(73) Assignee: BSP Biological Signal Processing Ltd., Tel-Aviv (IL)

( * ) Notice: Subject to any disclaimer, the term of this patent is extended or adjusted under 35 U.S.C. 154(b) by 1550 days.

(21) Appl. No.: 11/579,273

(22) PCT Filed: May 1, 2005

(86) PCT No.: PCT/IL2005/000457
§ 371 (c)(1),
(2), (4) Date: Nov. 2, 2007

(87) PCT Pub. No.: WO2005/104937
PCT Pub. Date: Nov. 10, 2005

(65) Prior Publication Data
US 2008/0194978 A1 Aug. 14, 2008

Related U.S. Application Data

(60) Provisional application No. 60/626,436, filed on Nov. 10, 2004, provisional application No. 60/567,306, filed on May 1, 2004.

(51) Int. Cl.
*A61B 5/04* (2006.01)
*A61B 5/0472* (2006.01)

(52) U.S. Cl.
CPC .................................. *A61B 5/0472* (2013.01)
USPC .......................................... 600/509; 600/516

(58) Field of Classification Search
USPC .................. 600/508–510, 512, 515–519, 521
See application file for complete search history.

(56) References Cited

U.S. PATENT DOCUMENTS

| 4,422,459 A | 12/1983 | Simson |
| 5,046,504 A | 9/1991 | Albert et al. |
| 5,117,833 A | 6/1992 | Albert et al. |
| 5,348,020 A | 9/1994 | Hutson |
| 5,655,540 A | 8/1997 | Seegobin |
| 5,954,664 A | 9/1999 | Seegobin |
| 6,035,231 A | 3/2000 | Sornmo et al. |

(Continued)

FOREIGN PATENT DOCUMENTS

| WO | WO 03/082077 | 10/2003 |
| WO | WO 2005/104937 | 11/2005 |

OTHER PUBLICATIONS

International Preliminary Report on Patentability Dated Nov. 9, 2006 From the International Bureau of WIPO Re.: Application No. PCT/IL2005/000457.

(Continued)

*Primary Examiner* — Carl H Layno
*Assistant Examiner* — Jessica Anthony

(57) ABSTRACT

An apparatus for QRS waveform quantifying, comprising: an input unit, for receiving one or more high frequency (HF) range QRS complexes from one or more ECG leads, a primary analyzer, for calculating a primary index from the high frequency (HF) range QRS complex, and a secondary analyzer, connected after the primary analyzer, for deriving a secondary index from the primary index, thereby to provide a quantification of QRS complexes.

22 Claims, 15 Drawing Sheets
(1 of 15 Drawing Sheet(s) Filed in Color)

(56) References Cited

U.S. PATENT DOCUMENTS

| | | | |
|---|---|---|---|
| 7,239,988 B2 | 7/2007 | Hasson et al. | |
| 2003/0013978 A1 | 1/2003 | Schlegel et al. | |
| 2003/0208129 A1* | 11/2003 | Beker et al. | 600/509 |
| 2004/0039292 A1* | 2/2004 | Schlegel et al. | 600/509 |
| 2004/0230130 A1* | 11/2004 | Kuo et al. | 600/515 |

OTHER PUBLICATIONS

Translation of the Office Action Dated Oct. 24, 2008 From the State Intellectual Property Office of the People's Republic of China Re.: Application No. 200580022577.1.
Response Dated Apr. 29, 2010 to Communication Pursuant to Article 94(3) EPC Dated Oct. 29, 2009 From the European Patent Office Re.: Application No. 05737629.5.
Communication Pursuant to Article 94(3) EPC Dated Oct. 29, 2009 From the European Patent Office Re.: Application No. 05737629.5.
International Search Report and the Written Opinion Dated Oct. 4, 2005 From the International Searching Authority Re.: PCT/IL05/00457.
Office Action Dated Oct. 27, 2009 From the Israel Patent Office Re.: Application No. 178997 and Its Translation Into English.
Translation of Office Action Dated Sep. 25, 2009 From the State Intellectual Property Office of the People's Republic of China Re.: Application No. 200580022577.1.
Translation of Notice of Reason for Rejection Dated Nov. 19, 2010 From the Japanese Patent Office Re. Application No. 2007-512717.
Response Dated Jul. 18, 2011 to Office Action of May 25, 2011 From the State Intellectual Property Office of the People's Republic of China Re.: Application No. 200580022577.1.

Abboud "High-Frequency Electrocardiogram Analysis of the Entire QRS in the Diagnosis and Assessment of Coronary Artery Disease", Progress in Cardiovascular Diseases, XXXV(5): 311-328, Mar./Apr. 1993.
Abboud et al. "Analysis of High Frequency Mid-QRS Potentials Vs. ST Segment and T Wave Analysis for the Diagnosis of Ischemic Heart Disease", Computers in Cardiology, 30: 813-814, 2003.
Beker et al. "Analysis of High Frequency QRS Potential During Exercise Testing in Patients With Coronary Artery Disease and in Healthy Subjects", PACE, 19(Pt.I): 2040-2050, Dec. 1996.
Requisition by the Examiner Dated Mar. 14, 2012 From the Canadian Intellectual Property Office Re. Application No. 2,565,192.
Communication Pursuant to Article 94(3) EPC Dated Jul. 6, 2012 From the European Patent Office Re. Application No. 05737629.5.
Examination Report Dated Jul. 20, 2012 From the Government of India, Patent Office, Intellectual Property Building Re. Application No. 4409/CHENP/2006.
Office Action Dated Sep. 24, 2012 From the Israel Patent Office Re. Application No. 178997 and Its Translation Into English.
Supplementary Partial European Search Report Dated Sep. 15, 2008 From the European Patent Office Re.: Application No. 05737629.5.
Translation of Office Action Dated Oct. 24, 2008 From the State Intellectual Property Office of the People's Republic of China Re.: Application No. 200580022577.1.
Yakubo et al. "Intra-QRS High-Frequency ECG Changes With Ischemia. Is It Possible to Evaluate These Changes Udsing the Signal-Averaged Holter ECG in Dogs?", Journal of Electrocardiology, XP004876800, 28(Suppl.): 234-238, Jan. 1, 1995. Abstract.
Translation of Office Action Dated May 25, 2011 From the State Intellectual Property Office of the People's Republic of China Re.: Application No. 200580022577.1.

* cited by examiner

APPARATUS AND METHOD FOR ANALYSIS OF HIGH FREQUENCY QRS COMPLEXES

RELATED APPLICATIONS

This application is a National Phase Application of PCT Patent Application No. PCT/IL2005/000457 having International Filing Date of May 1, 2005, which claims the benefit of U.S. Provisional Patent Application No. 60/626,436 filed on Nov. 10, 2004, and U.S. Provisional Patent Application No. 60/567,306 filed on May 1, 2004. The contents of the above Applications are all incorporated herein by reference.

FIELD AND BACKGROUND OF THE INVENTION

The present invention relates to medical instruments, and more particularly, but not exclusively to medical instruments for the detection and analysis of High Frequency ECG (electrocardiograph or "ECG") signals.

ECG describes the electrical activity of the complex of muscles that make up the different chambers of the heart. An ECG signal is recorded by body surface electrodes or implantable electrodes that measure the change in electrical potentials over the body due to the propagating electrical activation in the heart.

The ECG signal is a vector, that is to say it has directional properties. The different parts of the heart are at different locations, and signal propagation across the body is slow relative to the rate of events in the ECG, so that the overall waveform seen at different locations shows the different components of the overall ECG signal in different relationships with the other components.

Traditionally, up to ten detector electrodes are used, positioned at selected locations, so as to capture what is known as a 12-lead electrocardiogram. The basic ECG is captured by a single lead or electrode.

FIG. 1 depicts a typical ECG signal waveform, acquired by such an electrode. The waveform is generally divided into the following components as illustrated. The P wave 101, describes the depolarization of the atria, the QRS complex 103, describes ventricular depolarization, and the T wave 105, describes ventricular repolarization. Irregularity in these components is taken as a sign of heart problems.

ECG signal acquisition is most commonly performed while the person being monitored is at rest. However, since physical stress is known to introduce features into the ECG signal indicative of coronary artery disease (CAD) not present in signals obtained at rest, an ECG signal may also be obtained from a subject during a stress test comprising phases of rest, exercise and recovery from exercise. Certain medical procedures, especially catheterization of coronary arteries, are performed while the ECG signal is continuously monitored in order to ascertain the heart condition during the procedure.

Information related to the heart activity is extracted by means of ECG inspection and analysis, which concentrates on what is known as the P-QRS-T segment of the signal, as shown in FIG. 1. With the exception of the identification and interpretation of cardiac arrhythmias, most of the commonly used diagnostic aids based on ECG data, such as an S-T segment 111 shift, prolonged and bizarre QRS complex 103 patterns, or T wave 105 inversion—as indicated by their names—are related primarily to inspection of the P-QRS-T segment of the signal.

The significant frequency range of the ECG signals was traditionally considered to be from 0.05 Hz to 100 Hz. Although many common diagnostic methods are based solely on information contained in the 0.05 Hz-100 Hz frequency range, valuable information is known to be found in higher frequencies in the range of 150 Hz-250 Hz.

In "High-Frequency Electrocardiogram Analysis of the Entire QRS in the Diagnosis and Assessment of Coronary Artery Disease" article, published in the Progress in Cardiovascular Diseases journal, Vol. XXXV, No. 5, March/April 1993, the contents of which are hereby incorporated by reference, Abboud et al describe a study of the correlation between a decrease in the high frequency component of the QRS complex of an ECG signal, and an ischemic condition of the heart. Abboud at all have defined a condition of reduced amplitude zone (RAZ), in which there is a deep trough in the center of the envelope of the high frequency QRS signal for animals and persons undergoing an ischemic event.

Reference is now made to FIG. 2 which is a comparative diagram that illustrates traditional ECG and high frequency ECG signals obtained during different stages of a stress test of an ischemic heart disease (IHD) patient 210, compared with traditional ECG and high frequency ECG signals obtained during different stages of a stress test of a healthy subject 220.

The upper part 210 of the figure represents a typical example of the ECG signal during different stages of a stress test of an ischemic patient. The first row in the figure indicates the heart rate. The second row presents the standard ECG signal and the third row presents the HF signal. The HF signal shows a significant change as the exercise test progresses. The marked decrease in the amplitude of the signal is particularly notable.

The lower part 220 of FIG. 2 represents a typical example of the ECG signal during a stress test for a healthy subject. As in upper part 210, it is possible to follow the evolution of both the standard ECG and the HF signals during the test. Unlike Upper part 210, no significant change in the amplitude of the HF signal can be detected, indicating that no ischemic episode has occurred.

The problem posed by the present inventors was how to distinguish in automatic manner between the case of upper part 210 and lower part 220.

US Patent Applications 20030013978 by Schlegel et al. and 20040039292 by Schlegel et al. disclose RAZ analysis of the high frequency waveform.

The high frequency ECG signal is more difficult to process compared to the standard low frequency ECG signal, obtained in the range of 0.05-100 Hz. While the low frequency signal level is located in the millivolt range, the high frequency signal level is up to three orders of magnitude lower in voltage, and is highly sensitive to the fitness of the electrode-body contact and variations in such contacts during the ECG signal acquisition. Furthermore, motion of the body organs and muscles, especially while performing a stress test, reduces further the high frequency signal to noise ratio.

U.S. Pat. No. 7,151,957 to Beker et al., the contents of which are hereby incorporated by reference, discloses methods of high frequency waveform averaging to obtain an improved signal to noise ratio from such a signal.

Beker et al ("Analysis of High Frequency QRS Potential during Exercise Testing Patients with Coronary Artery Disease and in Healthy Subjects", Biomedical Engineering Department, Faculty of Engineering, Tel-Aviv University, 1995), and Abboud et al (Analysis of High Frequency Mid-QRS Potentials vs ST segment and T Wave Analysis for the Diagnosis of Ischemic Heart Disease, IEEE Computers in Cardiology 2003; 30:813-814), the contents of which are hereby incorporated by reference, showed that a decrease of the high frequency signal of the QRS complex during exercise test may serve as an indicator for an on-line early detection of ischemic pathologies. However, no details and no teaching were provided regarding the specifics of the signal processing, nor is there any disclosure of how the results can be analyzed to discriminate between sick and healthy subjects.

Simpson, in U.S. Pat. No. 4,422,459, teaches a system which analyzes only the late portion of the QRS interval and early portion of the ST segment, and in an off-line fashion (i.e. from previously stored data) to indicate cardiac abnormalities, in particular the propensity for cardiac arrhythmia. The late portion of a QRS waveform of a post myocardial infarction patient contains a high frequency (40 Hz-250 Hz) signal tail which is indicative of a tendency toward ventricular tachycardia. The system in Simpson digitally processes and filters a QRS signal in a reverse time manner to isolate the high frequency tail and avoid any filter ringing which would otherwise hide the signal. In order to carry out such reverse processing, Simpson presupposes that the raw data is stored. Otherwise it would not be possible to carry out processing in reverse time order.

Albert et al., U.S. Pat. No. 5,117,833, partially focuses on analyzing signals within the mid-portion of the QRS interval for the indication of cardiac abnormality. The system of Albert et al. uses a previously known technique of building up data points to derive an average of heartbeat characteristics in order to enhance signal to noise ratio. Data are collected and filtered and then stored for subsequent analysis. Thus, the system does not teach a cardiac monitor which provides the data analysis immediately from the data derived from a patient.

Albert et al., U.S. Pat. No. 5,046,504, similarly teaches the acquisition of QRS data and subsequent analysis. Routine calculations are performed from the data previously calculated and stored. Further, Albert teaches producing a set of digital spectrum values representative of an approximate power density spectrum at each of a large number of generally equally spaced sampling time intervals of the ECG waveform.

Seegobin, in U.S. Pat. Nos. 5,655,540 and 5,954,664, provides a method for identifying coronary artery disease. The method relies on a previously formed database of high and low frequency ECG data taken from known healthy and diseased subjects. Comparison of the data leads to a "Score" component, indicating deviation of the ECG data from the norm. This reference is calculation intensive, and does not suggest monitoring the condition of a patient, but rather is utilized as an off-line diagnostic tool.

Hutson, U.S. Pat. No. 5,348,020, teaches a technique of near real-time analysis and display. The technique includes inputting ECG data from multiple, sequential time intervals and formatting those data into a two-dimensional matrix. The matrix is then decomposed to obtain corresponding singular values and vectors for data compression. The compressed form of the matrix is analyzed and filtered to identify and enhance ECG signal components of interest. As with other systems, this reference focuses on late potentials, a fraction of the QRS interval, as the tool to identify cardiac disease.

There is thus a widely recognized need for, and it would be highly advantageous to have an ECG system and method for the detection and analysis of heart disorder, for example ischemic events, which is devoid of the above limitations.

SUMMARY OF THE INVENTION

According to a first aspect of the present invention there is provided apparatus for QRS waveform quantifying, comprising:

an input unit, for receiving at least one high frequency (HF) range QRS complex from at least one ECG lead;

a primary analyzer, associated with the input unit, for calculating a primary index from the at least one high frequency (HF) range QRS complex, and a secondary analyzer, connected after the primary analyzer, for deriving a secondary index from the primary index, thereby to provide a quantification of QRS complexes.

Preferably, the primary index is a statistical function of the at least one QRS complex.

Preferably, the primary index is at least one of a group comprising:

an RMS level of at least one HF QRS complex,
a standard deviation within an HF QRS complex,
a standard deviation over a plurality of HF QRS complexes,
a function of an envelope of an HF QRS complex,
a function of an envelope of a plurality of HF QRS complexes,
an envelope maximum over an HF QRS complex,
an envelope maximum over a plurality of HF QRS complexes,
an envelope width of an HF QRS complex,
an envelope width over a plurality of HF QRS complexes,
a cross-correlation value of the HF QRS complex with a template waveform, and
derivations of any one thereof.

Preferably, the secondary index is a running average of the primary index.

Preferably, the secondary index is a function of:

(a) a first primary index calculated by the primary analyzer from a first high frequency (HF) range QRS complex received at a first time period and (b) a second primary index calculated by the primary analyzer from a second high frequency (HF) range QRS complex received at a second time period.

Preferably, the secondary analyzer is operable to use the secondary index to indicate at least one of the presence and severity of an ischemic event or an ischemic heart condition or ischemic heart disease.

Preferably, at least one of the primary analyzer and the secondary analyzer is configured to commence the calculating or the deriving respectively while the input unit continues to receive data, thereby providing an on-line quantification.

According to a second aspect of the present invention there is provided apparatus for QRS waveform quantifying, comprising:

an input unit, for receiving at least one high frequency (HF) range QRS complex from at least one ECG leads; and a primary analyzer, associated with the input unit, for calculating a primary index for the high frequency (HF) range QRS complex, the primary analyzer being configured to use a standard deviation (STD) within the at least one high frequency QRS complex to derive the primary index.

Preferably, the primary index is derived from an ECG signal of a single lead, from which a plurality of the QRS complexes are obtained.

Preferably, the primary index is derived from a plurality of ECG signals taken from a plurality of ECG leads of a given patient.

The apparatus may comprise a secondary analyzer, connected after the primary analyzer, for deriving a secondary index from the primary index, thereby to provide a quantification of QRS waveforms.

Preferably, the secondary analyzer is further configured to define a moving average of the index.

Preferably, the primary analyzer is operable to use the primary index to indicate at least one of the presence and severity of an ischemic event or an ischemic heart conditions or ischemic heart disease.

According to a third aspect of the present invention there is provided apparatus for QRS waveform quantifying, comprising:

an input unit, for receiving a plurality of high frequency (HF) range QRS complexes of ECG signals as respective sets of amplitude values aligned over a time frame comprising time units such that there are a plurality of amplitude values for each time unit;

a reduction unit, associated with the input unit, for removing at least one outward amplitude value for any given time unit from the sets;

an analyzer, associated with the reduction unit, for calculating an overall index over the sets, using respective remaining amplitude values.

Preferably, the complexes are derived from separate ECG signal leads.

Alternatively, the complexes are derived from a single ECG signal lead.

Preferably, the removing comprises removing a plurality of amplitude values.

Preferably, the removing comprises removing all but a median amplitude value.

Preferably, the respective sets of amplitude values comprise derived indices of respective QRS complexes, such that the overall index is a secondary index.

Preferably, the reduction unit is configured to remove any amplitude value lying outside a region defined by a statistical function of the amplitude values.

Preferably, the statistical function is a standard deviation.

Preferably, the analyzer is operable to use the index to indicate at least one of the presence and severity of an ischemic event or an ischemic heart condition or ischemic heart disease.

According to a fourth aspect of the present invention there is provided apparatus for QRS waveform quantifying, comprising:

an input unit, for receiving a plurality of high frequency (HF) range QRS complexes obtained from a plurality of ECG leads at different locations on a subject;

an alignment unit for aligning the complexes, so that complexes derived from different leads but at the same time are associated together, and a primary analyzer, associated with the alignment unit, for calculating a primary index to provide a single quantification of the associated complexes.

Preferably, the primary index is a statistical function derived from the associated complexes.

The apparatus may comprise a secondary analyzer connected after the primary analyzer for calculating a secondary index at least indirectly from the primary index.

Preferably, the secondary index is a running average of the primary index.

Preferably, the secondary index is a function of a first primary index calculated from a first high frequency (HF) range QRS complex inputted at a first time period and a second primary index calculated from a second high frequency (HF) range QRS complex inputted at a second time period.

The apparatus may comprise a reduction unit associated with the alignment unit, for excluding outermost points from the associated complexes per predetermined unit time intervals.

Preferably, the primary analyzer is operable to use the primary index to indicate at least one of the presence and severity of ischemic events or ischemic heart conditions or ischemic heart disease.

Preferably, the secondary analyzer is operable to use the secondary index to indicate at least one of the presence and severity of ischemic events or ischemic heart conditions or ischemic heart disease.

According to a fifth aspect of the present invention there is provided apparatus for QRS waveform quantifying, comprising:

An input unit, for receiving a plurality of high frequency (HF) range QRS complexes from at least one ECG signal; and a primary analyzer, associated with the input unit, for calculating a primary index for the plurality of high frequency (HF) ECG range QRS complexes, the calculating comprising using an envelope of the QRS complexes. Preferably, the primary analyzer is configured to use a maximum of the envelope within a given time frame from which to derive the index.

Preferably, the analyzer is configured to use a width of the envelope within a given time frame, from which to derive the index.

Preferably, the analyzer is configured to use a statistical function of the envelope within a given time frame, from which to derive the index.

Preferably, the high frequency range includes frequencies above 100 Hz.

Preferably, the high frequencies range includes the 150 Hz-250 Hz range.

Preferably, the index is presented to a user in a two dimensional time-amplitude graph.

Preferably, the analyzer is operable to use the index to indicate at least one of the presence and severity of ischemic events.

Preferably, the index is a standard deviation and wherein the analyzer is configured to use an increase in the index to indicate the presence of ischemia.

The apparatus is preferably further configured to issue an alarm signal upon detection of an indication of ischemia.

According to a further aspect of the present invention there is provided a method for QRS waveform quantifying, comprising:

receiving at least one high frequency (HF) range QRS complex from at least one ECG leads;

calculating a primary index from the at least one high frequency (HF) range QRS complex, and deriving a secondary index from the primary index, thereby to provide a quantification of QRS complexes.

Preferably, the primary index is a statistical function of at least one QRS complex.

Preferably, the primary index is at least one of a group comprising:

an RMS level of at least one HF QRS complex,
a standard deviation within an HF QRS complex,
a standard deviation over a plurality of HF QRS complexes,
a function of an envelope of an HF QRS complex,
a function of an envelope of a plurality of HF QRS complexes,
an envelope maximum over an HF QRS complex, an envelope maximum over a plurality of HF QRS complexes,
an envelope width over an HF QRS complex,
an envelope width over a plurality of HF QRS complexes,
a cross-correlation value of the HF QRS complex with a template waveform, and
a derivation of any one thereof.

Preferably, the secondary index is a running average of the primary index.

According to a sixth aspect of the present invention there is provided a method for QRS waveform quantifying, comprising:
receiving at least one high frequency (HF) range QRS complex from at least one ECG leads;
calculating an index for the high frequency (HF) range QRS complex, the calculating comprising using a standard deviation (STD) within the high frequency QRS complex to derive the index.

According to a seventh aspect of the present invention there is provided a method for QRS waveform quantifying, comprising:
receiving a plurality of high frequency (HF) range QRS complexes of ECG signals as respective sets of amplitude values aligned over a time frame comprising time units such that there are a plurality of amplitude values for each time unit;
removing at least outer amplitude values for any given time unit from the sets;
calculating an overall index over the sets, using respective remaining amplitude values.

Preferably, the removing comprises removing a plurality of outer amplitude values.

Alternatively, the removing comprises removing all but a median amplitude value.

Preferably, the respective sets of amplitude values comprise derived indices of respective QRS complexes, such that the overall index is a secondary index.

The method may comprise removing any points lying outside a region defined by a statistical function of the amplitude values.

Preferably, the statistical function is a standard deviation.

According to an eighth aspect of the present invention there is provided a method for QRS waveform quantifying, comprising:
receiving a plurality of high frequency (HF) range QRS complexes obtained from a plurality of ECG leads at different locations on a single subject;
aligning the complexes, so that complexes derived from different leads but at the same time are associated together, and
calculating a primary index to provide a single quantification of the associated complexes.

Preferably, the primary index is a statistical function derived from the associated complexes.

The method may comprise calculating a secondary index at least indirectly from the primary index.

Preferably, the secondary index is a running average of the primary index.

The method may comprise excluding outermost points from the associated complexes per predetermined unit time intervals.

According to a ninth aspect of the present invention there is provided a method for QRS waveform quantifying, comprising:
receiving a plurality of high frequency (HF) range QRS complexes from at least one ECG signal; and
calculating an index for the plurality of high frequency (HF) ECG range QRS complexes, the calculating comprising using an envelope of the QRS complexes.

The method may comprise using at least one of a group comprising:
a maximum of the envelope within a given time frame from which to derive the index,
a width of the envelope within a given time frame, from which to derive the index, and
a statistical function of the envelope within a given time frame, from which to derive the index.

Preferably the index is a standard deviation, so that the method further comprises using an increase in the index to indicate the presence of ischemia.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 depicts a typical ECG signal waveform.

FIG. 2 illustrates traditional ECG and high frequency ECG signals obtained during different stages of a stress test.

FIG. 3 is a block diagram of an apparatus for QRS waveform quantifying according to a preferred embodiment of the present invention.

FIG. 4 is a block diagram of a second apparatus for QRS waveform quantifying according to a preferred embodiment of the present invention.

FIG. 5 is a block diagram of a third apparatus for QRS waveform quantifying according to a preferred embodiment of the present invention.

FIG. 6 is a block diagram of a fourth apparatus for QRS waveform quantifying according to a preferred embodiment of the present invention.

FIG. 7 is a block diagram of a fifth apparatus for QRS waveform quantifying according to a preferred embodiment of the present invention.

FIG. 8 is a flow diagram of a method for QRS waveform quantifying according to a preferred embodiment of the present invention.

FIG. 9 is a flow diagram of a second method for QRS waveform quantifying according to a preferred embodiment of the present invention.

FIG. 10 is a flow diagram of a third method for QRS waveform quantifying according to a preferred embodiment of the present invention.

FIG. 11 is a flow diagram of a fourth method for QRS waveform quantifying according to a preferred embodiment of the present invention.

Figure 12:
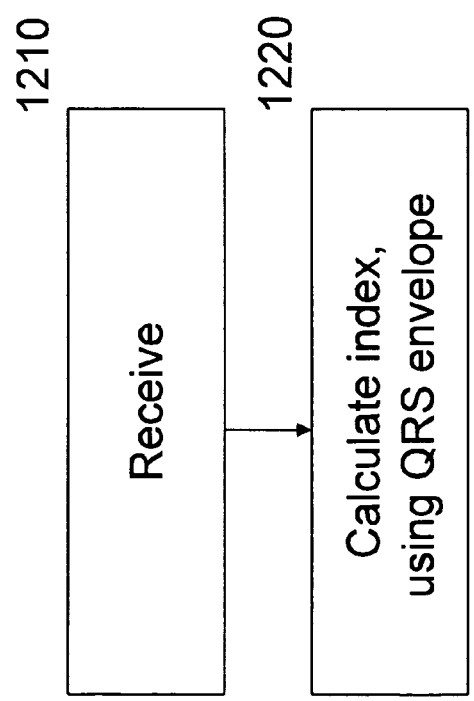

FIG. 12 is a flow diagram of a fifth method for QRS waveform quantifying according to a preferred embodiment of the present invention.

Figure 13:
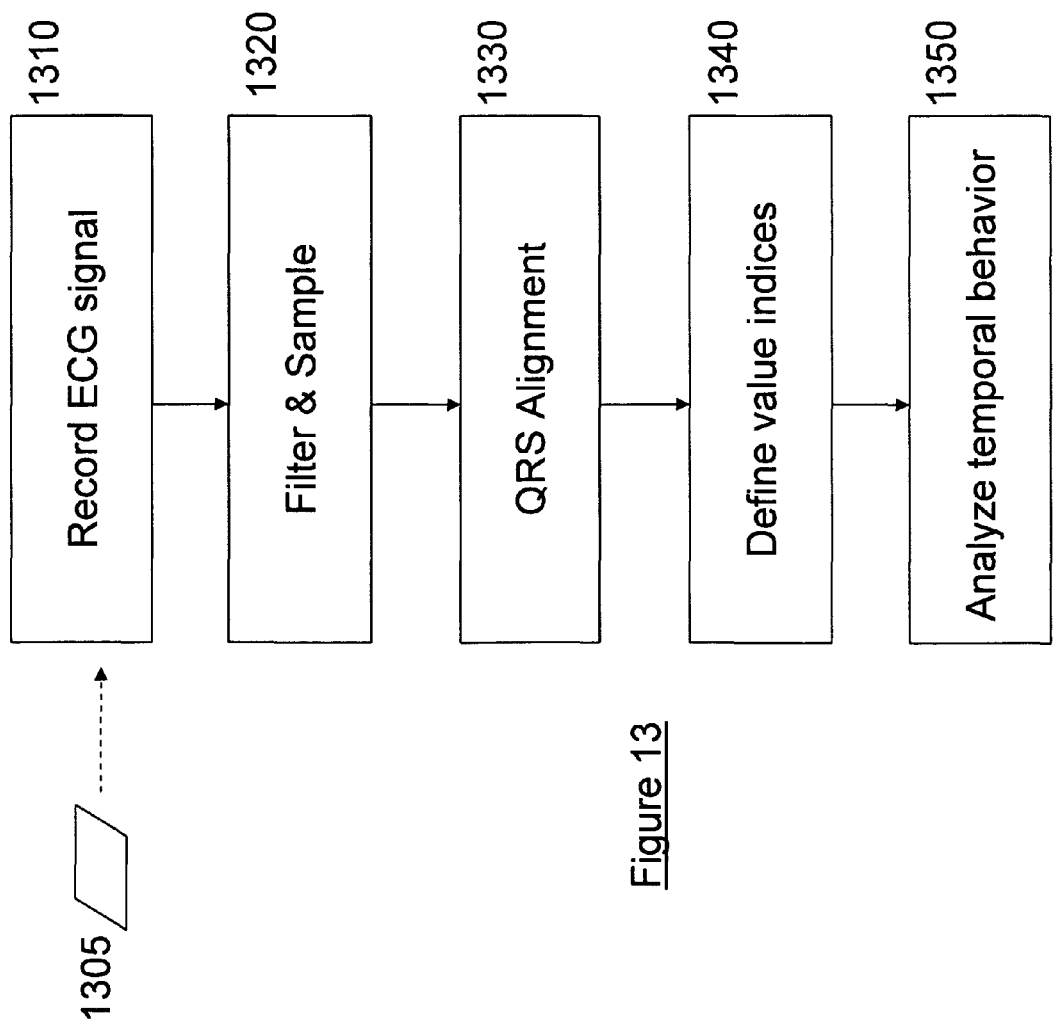

FIG. 13 is a flowchart of a method for detecting ischemic events, according to a preferred embodiment of the present invention.

Figure 14:
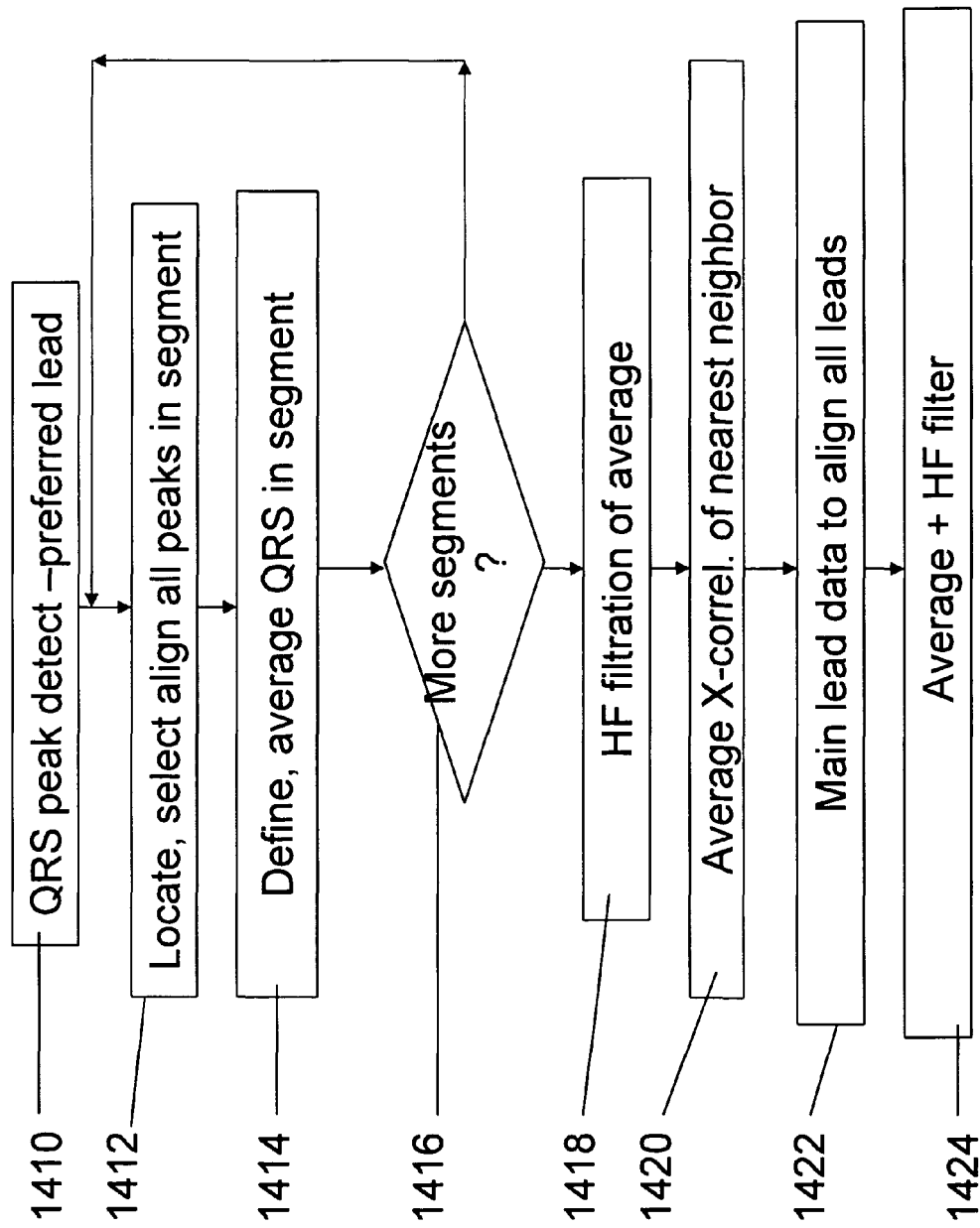

FIG. 14 is a flowchart showing some of the stages of FIG. 13 in greater detail.

Figure 15:
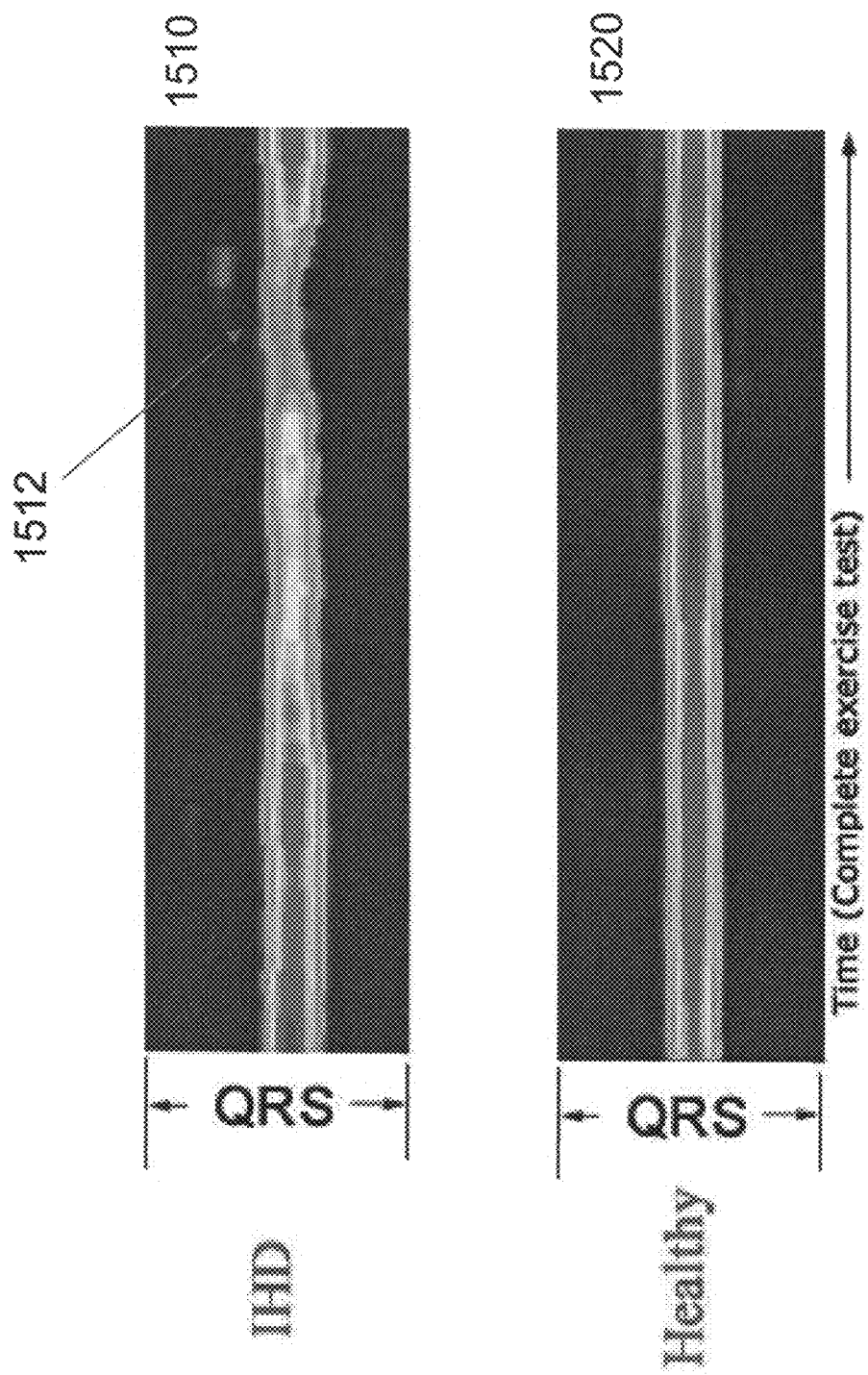

FIG. 15 is an exemplary time-amplitude graph for presenting waveform envelope indices, according to a preferred embodiment of the present invention.

DESCRIPTION OF THE PREFERRED EMBODIMENTS

The present embodiments comprise apparatus and methods for QRS waveform quantifying that may be utilized for detecting ischemic events.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 3:
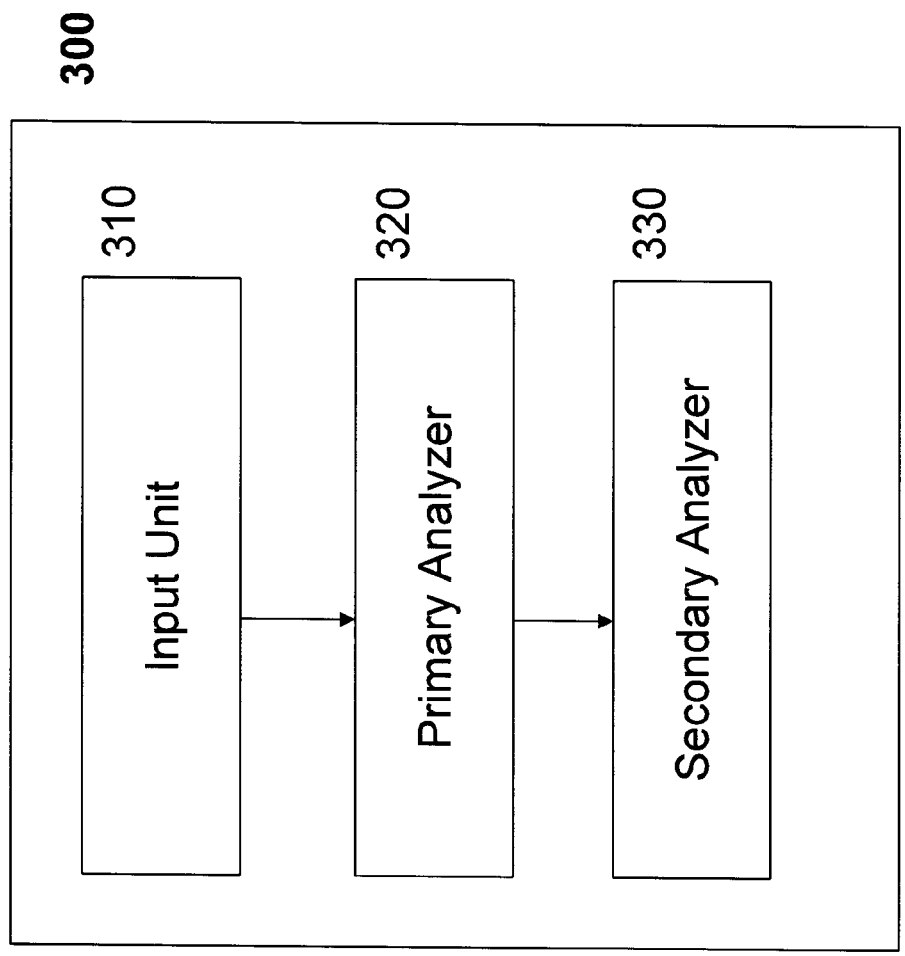

Reference is now made to FIG. 3, which is a block diagram of an apparatus for QRS waveform quantifying according to a preferred embodiment of the present invention.

Figure 1:
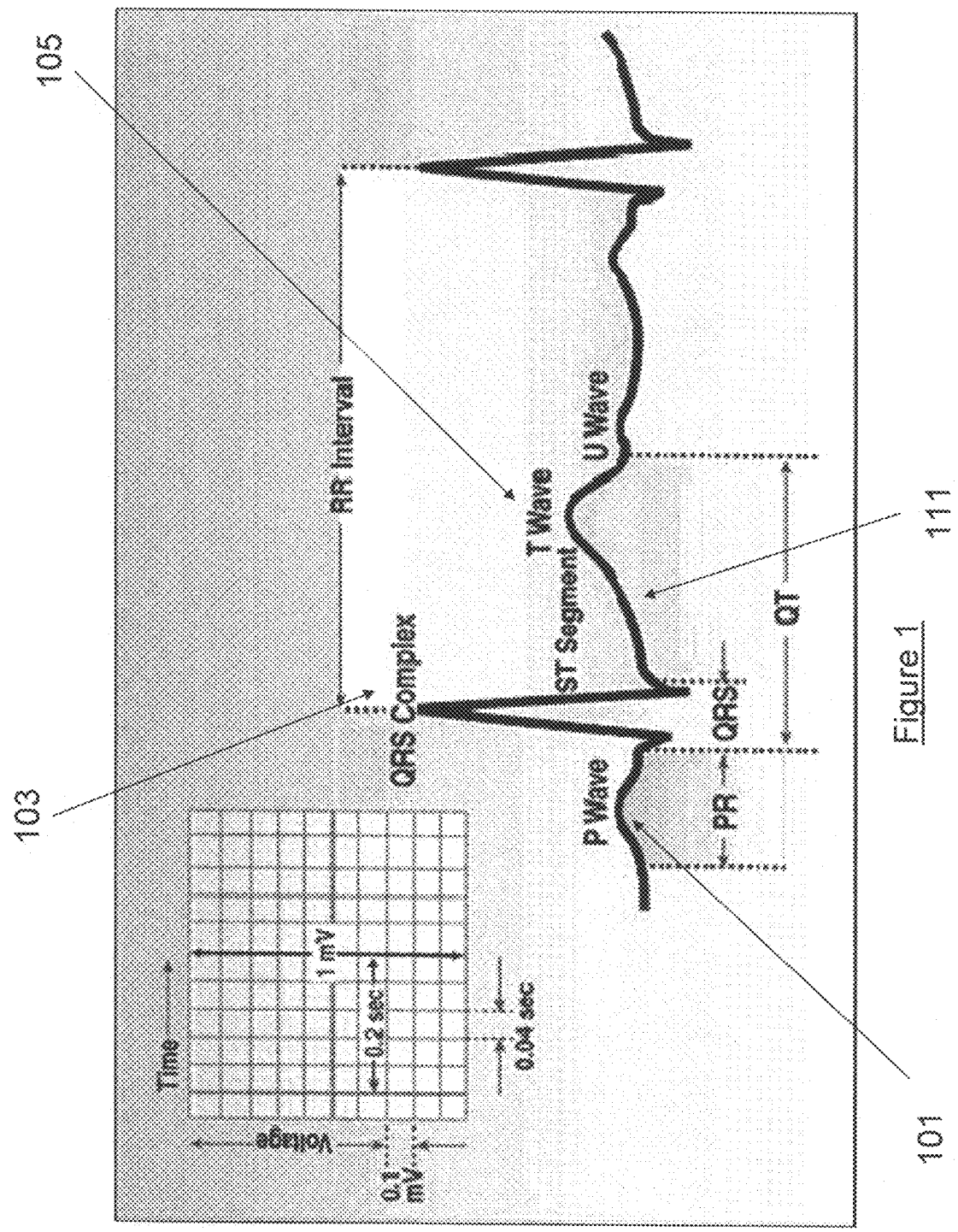
Figure 2:
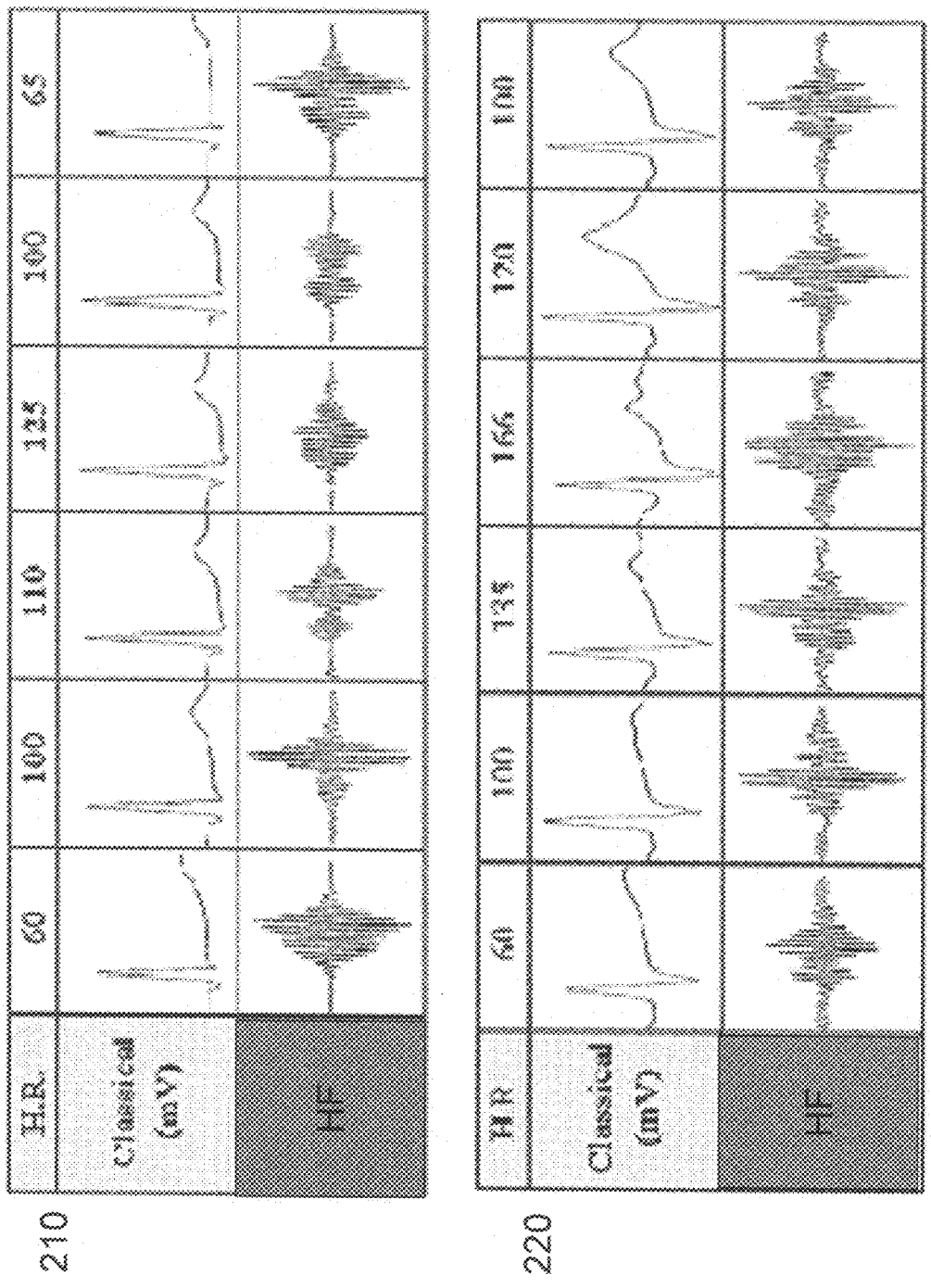

The apparatus 300 comprises: an input unit 310, for receiving high frequency (HF) range QRS complex(es) (HF-QRS complexes) from ECG lead(s). The HF QRS complexes are typically of the kind shown in FIG. 2 and the input unit includes the features necessary for obtaining such a signal, such as the appropriate filters and noise reduction circuitry, examples of which are detailed in applicant's above referenced U.S. Pat. No. 7,151,957. Apparatus 300 further comprises a primary analyzer 320, located after the input unit, which calculates a primary or first order index from the high frequency (HF) range QRS complexes. The primary index is preferably a direct quantification derived from the HF QRS complex and examples are given below. Connected after the primary analyzer is a secondary analyzer 330, which derives a secondary or second order index from the first order index. The secondary index may be derived from the primary index of a single complex or it may be derived from the primary indexes of several connected complexes. For example the connected complexes may be different complexes taken at the same time from different ECG leads. Alternatively the connected complexes may be taken from a single lead but at different times. In the general case, the secondary index is derived from a set of complexes taken at different times from different ECG leads.

The secondary index provides an overall quantification of the high frequency QRS complex or complexes from which it is derived.

In one embodiment, the primary index is a direct function of the HF QRS complex. In an alternative embodiment the primary index is a statistical function of the QRS complex. Examples of primary indices include the following: an RMS level of the HF QRS complex, a standard deviation within an HF QRS complex, a function of an envelope of an HF QRS complex, a function of an envelope of the QRS complexes, including an envelope maximum over one or more HF QRS complexes, an envelope width of an HF QRS complex, an envelope width over a plurality of HF QRS complexes, a cross-correlation value of the HF QRS complex with a template waveform, and derivations of any of these alternatives.

The second order index may be derived from the primary index. In one non-limiting embodiment, the second order index is a running average of the primary index.

In another embodiment, the second order index is a ratio of a primary index obtained at one time during a medical procedure (such as, but not limited to, stress test, or patient monitoring) to a primary index obtained at another, second time. Generally, the second order index is a function of primary indices of one or a plurality of different leads obtained at one or more times during a medical procedure, with or without primary indices of one or a plurality of different leads obtained at one or more times before and/or after the duration of the medical procedure.

Figure 4:
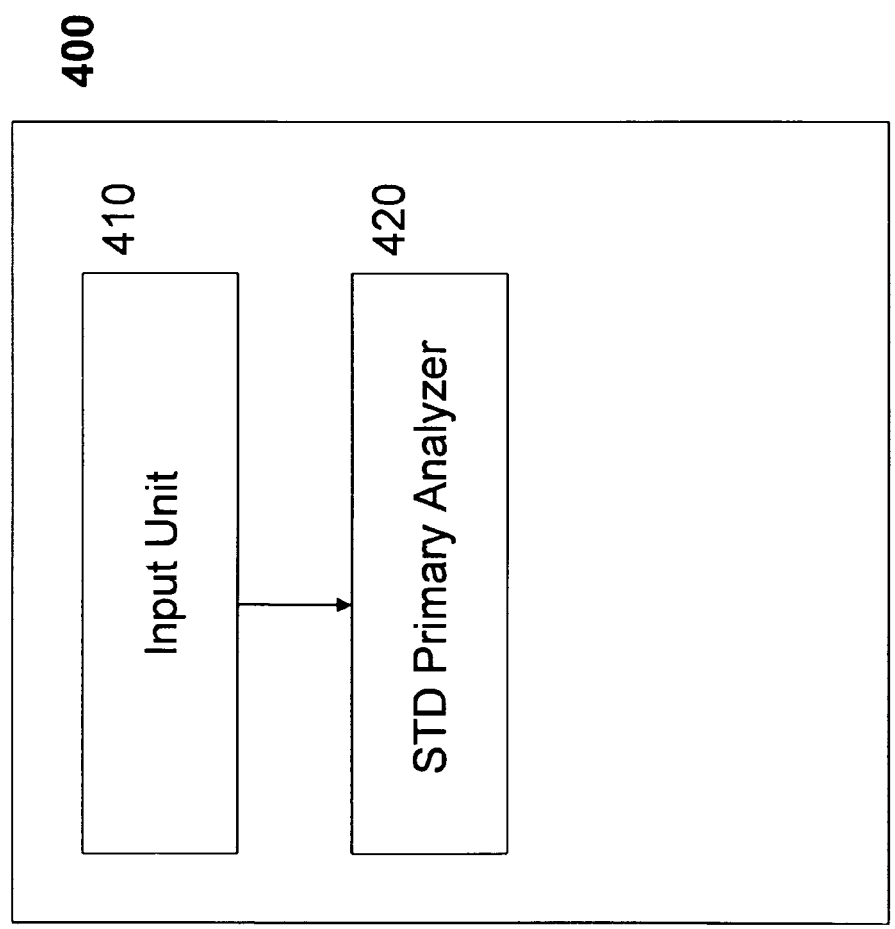

Reference is now made to FIG. 4, which is a block diagram of apparatus for QRS waveform quantifying according to a second preferred embodiment of the present invention.

The apparatus 400 comprises: an input unit 410, for receiving a high frequency (HF) range QRS complex(es) from one or more ECG leads, and a STD primary analyzer 420, which is connected to the input unit, for calculating an index for the high frequency (HF) range QRS complex(es). The analyzer 420 is configured to use a standard deviation (STD) within the high frequency QRS complex to derive the index.

The index may be derived from an ECG signal of a single lead from which a plurality of QRS complexes are obtained in a series. The index may alternatively be derived from ECG signals taken from a plurality of ECG leads located on a given patient in multi-lead ECG. The standard deviation may for example be calculated over all the complexes received simultaneously from the different leads and thus representing the same heart beat.

The analyzer 420 may be further configured to define a moving average of the above described index. The moving average would constitute a secondary or derived index. It is noted that the moving average is only an example of a derived index and many other derived indices may be used, several preferred examples of which are listed hereinbelow.

Figure 5:
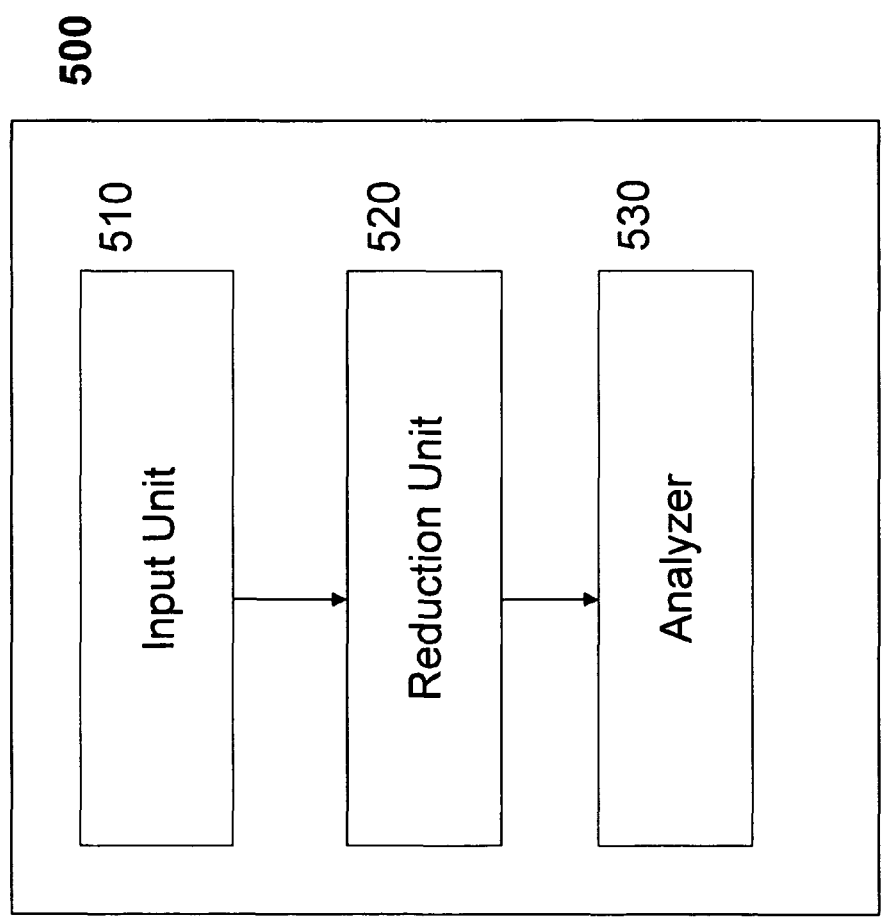

Reference is now made to FIG. 5, which is a block diagram of apparatus for QRS waveform quantifying according to a third preferred embodiment of the present invention.

The apparatus 500 comprises an input unit 510, which receives a plurality of wide band (WB) range QRS complexes of ECG signals. The signals may be in the form of amplitude values aligned over a time frame. Preferably there are several values per time interval, one value from each signal. Following the input unit is a reduction unit 520, which removes at least the outer values at each time interval. It is noted that at different time intervals, values from different complexes may be removed, so that overall a best behaved set of values is obtained, but no particular complex (or lead) is singled out for rejection.

Apparatus 500 further includes an analyzer 530, located after the reduction unit, which may extract the high frequency QRS component and analyze the result by calculating an overall index using the remaining values after reduction. As an alternative the input unit may carry out the extraction although certain processes such as alignment are preferably carried out on the wideband signal whereas other processes are carried out specifically on the high frequency QRS.

The QRS complexes may be derived from separate ECG signal leads. Alternatively, the QRS complexes may be derived from a single ECG signal. The QRS complexes may thus represent different time-frames of the same single ECG signal.

The removing of outer values may involve removing just the outermost values, say one highest value and one lowest value. Alternatively more than one highest and more than one lowest value may be removed. As a further alternative, all of the outer points may be removed to leave a single median point.

The sets of values on which removal is carried out may comprise values of the signals themselves or values of primary or secondary indices.

Rather than removing a given number of points, the reduction unit 520 may be configured to remove any points lying outside a region defined by a statistical function of the values. Optionally, the statistical function of the points may be a standard deviation (STD) function, so that the reduction unit may for example remove any points lying outside two standard deviations from an average.

Figure 6:
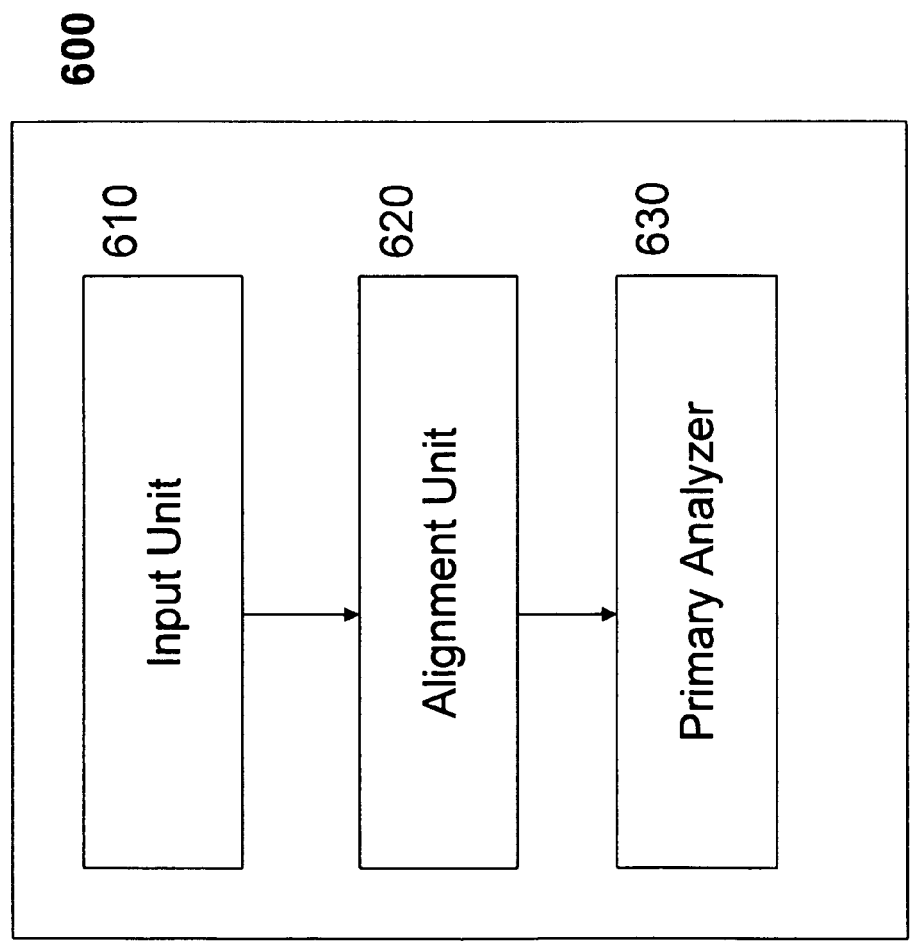

Reference is now made to FIG. 6, which is a block diagram of apparatus for QRS waveform quantifying according to a fourth preferred embodiment of the present invention.

Apparatus 600 comprises: an input unit 610, which receives wide band (WB) QRS complexes obtained from a plurality of ECG leads at different locations on the body of a single subject as described above. It further includes an alignment unit 620 for aligning the complexes, so that complexes derived from different leads but at the same time are associated together, and a primary analyzer 630, associated with the alignment unit, for extracting the HF QRS component for calculating a primary index to provide a single quantification of the associated complexes.

Optionally, the primary index may be a statistical function derived from the associated complexes.

The apparatus 600 may further comprise a secondary analyzer connected after the primary analyzer 630 for calculating a secondary or derived index from the primary index. Optionally, this secondary index is a running average of the primary index, however other secondary indices are possible and are described hereinbelow.

The apparatus 600 may further comprise a reduction unit associated with the alignment unit 620, for excluding outermost points from the associated complexes per predetermined unit time intervals.

Figure 7:
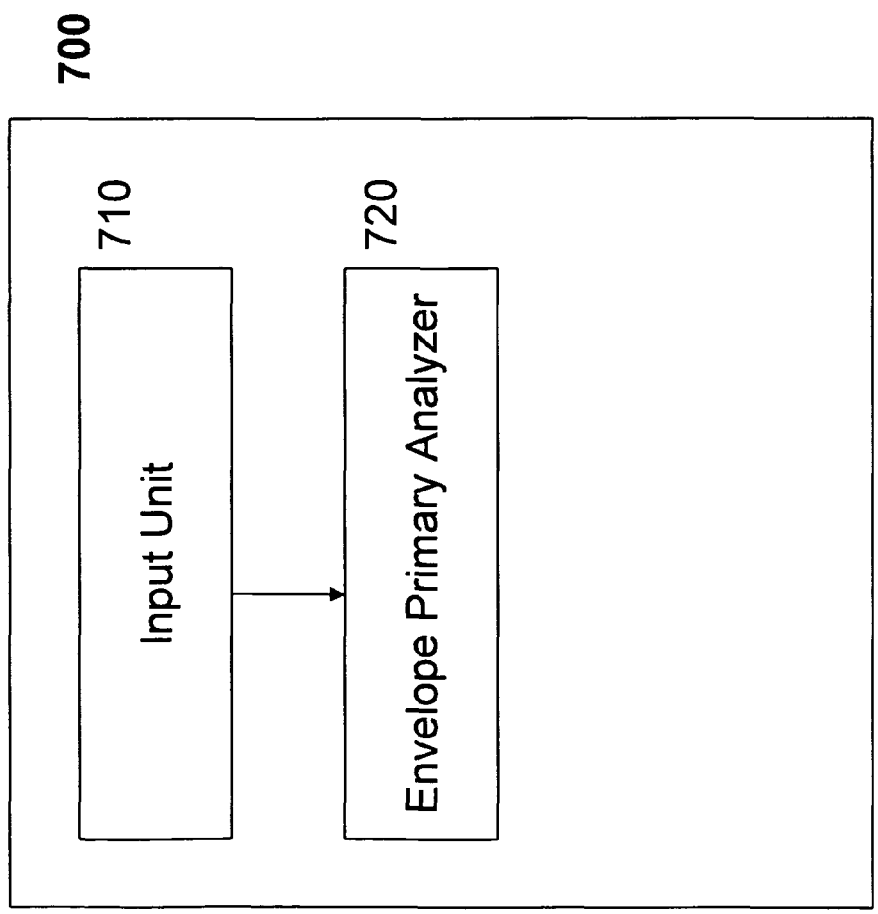

Reference is now made to FIG. 7, which is a block diagram of a further apparatus for QRS waveform quantifying according to a fifth preferred embodiment of the present invention.

Apparatus 700 comprises: An input unit 710, for receiving a plurality of high frequency (HF) range QRS complexes from ECG signal(s) as described above, and an envelope primary analyzer 720, connected to the input unit 710, for calculating an index for the plurality of high frequency (HF) ECG range QRS complexes.

The analyzer 720 may use an envelope of the QRS complexes. The analyzer 720 may be configured to use a maximum of the envelope within a given time frame from which to derive the index. The analyzer 720 may alternatively be configured to use a width of the envelope within a given time frame from which to derive the index. The analyzer 720 may alternatively be configured to use a statistical function of the envelope within a given time frame, from which to derive the index.

In the above, the high frequency QRS complex is as discussed in the glossary below. More generally it is that signal which is obtained when looking at signals above 100 Hz. More preferably, as presented in the glossary, the high frequency range is the 150 Hz-250 Hz range, which is especially significant as far as the detection of ischemic events in a subject is concerned.

The index may be presented to a user in a two dimensional time-amplitude graph. Preferably, the two dimensional time-amplitude graph is the Waveform Envelope Graph, described below.

Preferably, the analyzer 720 is operable to use the index to indicate the presence or severity of ischemic events. For example, the index may be a standard deviation and the analyzer 720 may be configured to use an increase in the index to indicate the presence of ischemia. Other optional parameters for detecting ischemic events, using a QRS waveform index are provided below. Preferably, the apparatus 700 is further configured to issue an alarm signal upon detection of an indication of ischemia. This alarm signal may include, but is not limited to a visual signal, a sound, a phone call to a physician or a nurse etc.

Figure 8:
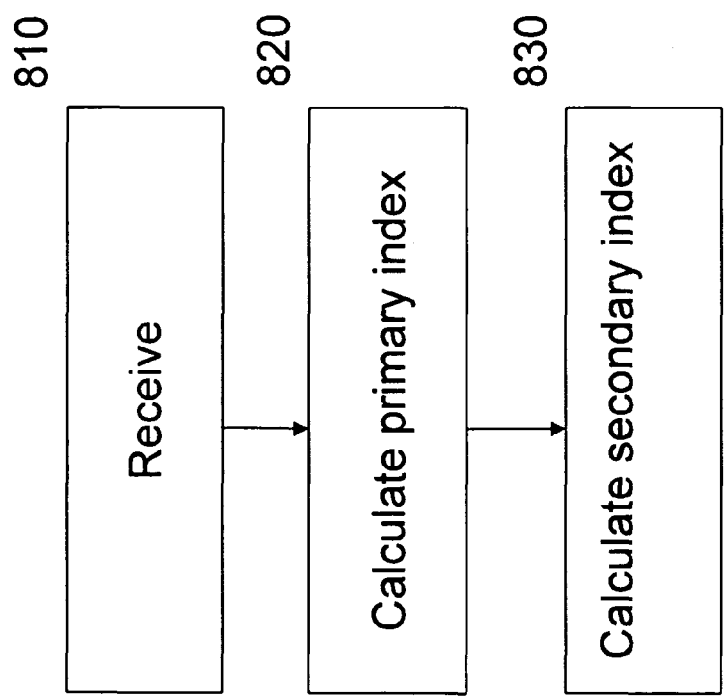

Reference is now made to FIG. 8, which is a flow diagram of a method for QRS waveform quantifying according to a preferred embodiment of the present invention.

In a first step, a high frequency (HF) range QRS complex (es) from an ECG lead(s) is received 810. Next, a primary index is calculated 820 from the high frequency (HF) range QRS complex(es). Finally, a second order index is derived in a stage 830 from the first index. The second order index provides a quantification of the QRS complexes.

The primary index may be a direct or a statistical function of the QRS complex(es). For example, the primary index may be one of the following: an RMS level of the HF QRS complex(es) or its envelope, a standard deviation within an HF QRS complex, a standard deviation over a plurality of HF QRS complexes, a function of an envelope of one or more HF QRS complexes, an envelope maximum over an HF QRS complex, an envelope maximum over one or more HF QRS complexes, an envelope width of one or more HF QRS complexes, a cross-correlation value of the HF QRS complex with a template waveform, and derivations of any of these alternatives.

Optionally, the secondary or second order index may be a running average of the primary or first order index.

Figure 9:
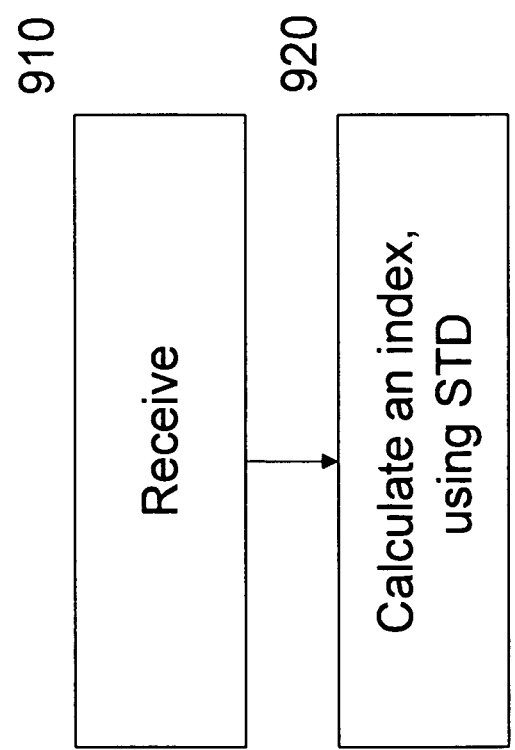

Reference is now made to FIG. 9, which is a flow diagram of a method for QRS waveform quantifying according to a further preferred embodiment of the present invention.

In a first stage, high frequency (HF) range QRS complex(es) are received from ECG lead(s) 910. In the second step, an index is calculated for the high frequency (HF) range QRS complex(es) 920. The index may be a standard deviation (STD) within the high frequency QRS complex(es). Alternatively the index may be a derivation of the standard deviation.

Figure 10:
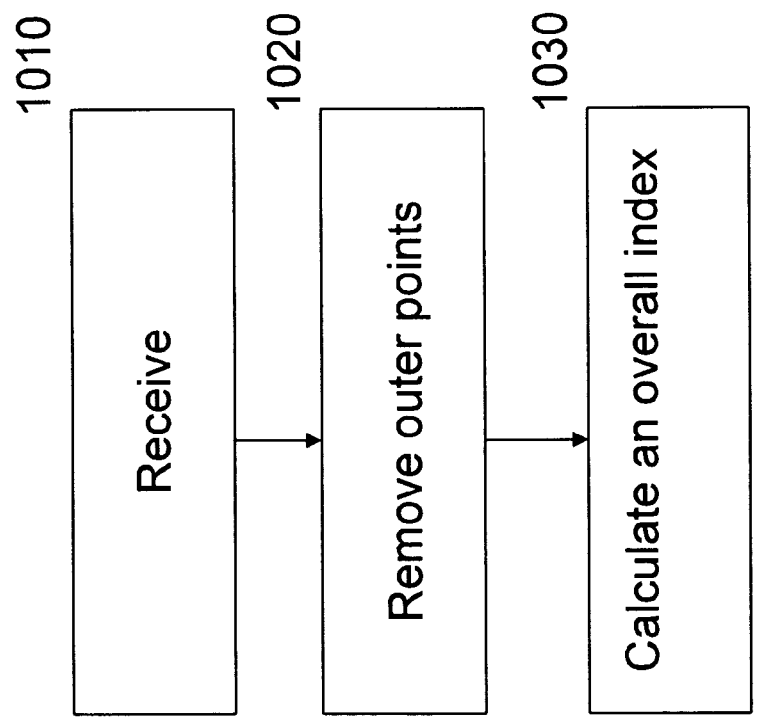

Reference is now made to FIG. 10, which is a flow diagram of a further method for QRS waveform quantifying according to a preferred embodiment of the present invention.

First of all, multiple wide band (WB) range QRS complexes of ECG signal graphs are received 1010 as amplitude values aligned over a time frame. For each time unit within the time frame there are separate values for each complex. Outer point(s) are then removed per time unit from the sets 1020. Finally, after extracting the HF components an overall index over all the sets is calculated 1030, using the respective remaining points.

The number of points removed may be varied. One may remove say the two most distant values from an average, or the highest value plus the lowest value or n most distant values or n highest values plus n lowest values. Alternatively, all values may be removed except for a single median value. As a further alternative it is possible to remove any points lying outside a region defined by a statistical function of the values. For example the statistical function is a standard deviation. All values lying outside say two standard deviations of a mean or median may for example be removed.

The values may be raw HF complex data values, or primary or other derived indices thereof, as preferred.

Figure 11:
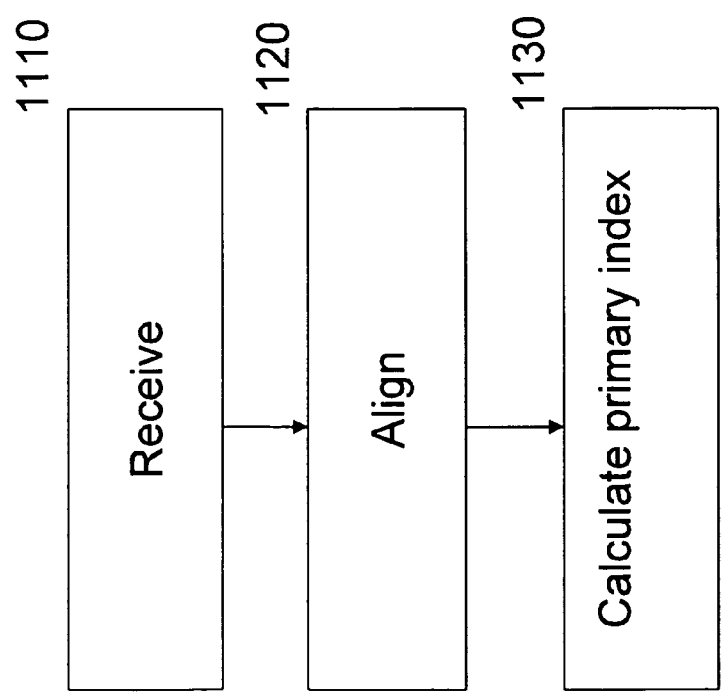

Reference is now made to FIG. 11, which is a flow diagram of a further method for QRS waveform quantifying according to a preferred embodiment of the present invention.

First of all, multiple wide band (WB) range QRS complexes, obtained from a plurality of ECG leads at different locations on the body of a single subject, are received 1110. Subsequently, the complexes are aligned 1120, so that complexes derived from different leads but at the same time are associated together. Then, after extracting the HF component, a primary index is calculated 1130, to provide a single quantification of the associated complexes.

The primary index may be a statistical function derived from the associated complexes. Optionally, the present method may further comprise calculating a secondary or other derived index from the primary index. For example, a secondary index may be calculated as a running average of the primary index.

Reference is now made to FIG. 12, which is a flow diagram of a fifth method for QRS waveform quantifying according to a preferred embodiment of the present invention.

In a first stage, a plurality of high frequency (HF) range QRS complexes are received from ECG signal(s) 1210, and then, an index is calculated 1220 for the plurality of high frequency (HF) ECG range QRS complexes. The calculating may comprise using an envelope of the QRS complexes.

The present method may comprise using at least one of the following: a maximum of the envelope within a given time frame from which to derive the index, a width of the envelope within a given time frame, from which to derive the index, and a statistical function of the envelope within a given time frame, from which to derive the index.

For example, the index may be a standard deviation. The method may further comprise using an increase in the index to indicate the presence of ischemia.

Reference is now made to FIG. 13, which is a flowchart of a method for detecting ischemic events, according to a preferred embodiment of the present invention.

In the first step, the ECG signal 1305 is recorded 1310. Next, the signal is sampled, as detailed further below. Next, QRS complex positions are detected in the signal. QRS complex detection may be done by any known in the art method. The detection process can be done independently on each lead. Alternatively, the detection involves having common QRS positions for all leads, and then verifying this position per lead, or accepting it automatically for each lead.

In step 1320, the present method applies high frequency (HF) filtering on the signal. Preferably, the high frequency range is as discussed in the glossary.

In step 1330, the QRS complexes are aligned with respect to each other within each ECG lead as well as between the different leads. QRS detection and alignment may be performed on the raw recorded signal, or preferably on the low frequency (0.05 Hz-100 Hz) filtered signal.

In step 1340, value indices are defined for the HF filtered signal. In a preferred embodiment of the present invention used with multiple lead ECG, the definition step involves obtaining a single index for all leads of the signal. The single index may be based on all of the leads or only on preferred leads. These indices may be defined using various methods, as described in detail below. Finally, the temporal behavior of the indices is analyzed 1350. Preferably, the analysis of the temporal behavior of the indices may help determine ischemic events in a subject.

In a preferred embodiment of the present invention, the present method further comprises a noise reduction step. This noise reduction step may be done by simple-averaging or weight-averaging the signal in the QRS positions. Alternatively, the reduction may be done using any known method.

Prior to the first stage the ECG signal is typically acquired (1305) by placing at least two electrodes on the body surface of a subject, as known in the art. Up to 10 or 12 electrodes may be positioned at specified points on the subject. Alternatively, implantable electrodes, or implantable cardiac devices containing electrodes, can be used. The electrode-provided signals are well synchronized. The standard ECG signal acquisition is usually performed using a band-pass filter that filters only frequencies in the range of 0.05 Hz-100 Hz.

In order to utilize the method, according to a preferred embodiment of the present invention, a wide band ECG signal may be acquired using a wider bandwidth filter that allows higher frequencies to be detected, e.g. a band-pass filter in the frequency range of 0.05 Hz-250 Hz.

The filtered electrical signal is digitally sampled at a sampling rate of at least twice the maximal frequency range, e.g. a sampling rate of 500 Hz or higher. Preferably, a sampling rate of 1000 Hz is used. A minimal sampling rate which is twice the maximum frequency of the signal, known in the art as the Nyquist rate, may help provide a signal without aliasing. Aliasing occurs when signal frequencies overlap because the sampling frequency is too low. Aliasing results in the presence of unwanted components in the reconstructed signal. Preferably, the sampling rate is adjustable, i.e. by controlling an adjustable analogue-to-digital (A/D) converter.

Alternatively, a wide-band input signal can be sampled at the sampling rate discussed above, and the sampled data can be digitally filtered later into the required band widths.

The sampled amplitudes of the ECG potential differences between certain pairs of electrodes, and/or other linear combinations of the potentials of the electrodes as known in the art, are thus recorded, together with a temporal reference indication as to the relative or absolute sampling time.

In a standard stress test the electrodes are attached to the patient, and following a short rest period the patient starts to walk on a tread-mill or ride a cycle ergometer (gymnastics bike) with the speed and stress (slope of the tread-mill, friction on the bike) being increased according to a specified protocol. The standard test lasts for about 10-20 minutes, or 600-1200 seconds, resulting in storage of 600,000-1,200,000 sampled amplitudes per lead.

Alternatively, the ECG signal may be monitored, for example, during a catheterization of the coronary arteries procedure, and sample recording may take place before, during and after performing an inflation of a balloon within the artery. In different medical settings, patients under observation, such as patients hospitalized in Critical Care Units, may also have their ECG signal continuously monitored for changes in their heart condition, and in such a case their ECG signal should be sampled as long as the monitoring proceeds. In the monitoring case, the sampled data is continuously analyzed on a segment by segment basis according to the procedure detailed below. Value index or indices are calculated for the analyzed HF-QRS waveforms, and a real-time alert is generated if the temporal behavior of the indices undergoes a change beyond a pre-defined absolute or relative limit or limits.

As described above, after the signal is recorded 1310, the signal is digitized (sampled) using an A/D converter and then bandpass filtered in stage 1320. Alternatively, the signal is bandpass filtered using appropriate hardware, and is then digitized. In stage 1330, QRS complexes are detected in the signal and alignment occurs. Step 1330 may start as soon as the sampling recording has lasted for a few seconds, preferably 10 seconds. Alternatively, this stage may be performed after the entire medical session, such as a stress test, has been completed.

If multiple ECG leads are sampled, QRS detection is preferably performed in more than one lead, for example three leads, more preferably in leads known to have the sharpest and highest amplitude R wave ("preferred leads"). QRS detection may be performed in any method known in the art, including, but not limited to, a search of amplitude maxima within the first few seconds of sampled amplitudes, followed by a validity check of nearest neighbor sampled points, as well as the waveform of the second derivative of the sampled signal in the vicinity of the maximal points. Alternatively, the sampled ECG signal may be cross-correlated with a QRS waveform template, and the temporal position of the maximum of the cross-correlation function can then be checked in the sampled ECG signal as a suspected QRS complex. An alternative method to cross-correlation for measuring waveform similarity could be a projection sum of absolute differences. Many other suitable methods are known in the art.

Reference is now made to FIG. 14, which is a simplified diagram illustrating in greater detail stages 1330 and subsequent stages of FIG. 13. The following discussion refers to both diagrams.

Following the QRS complex detection 1330, each of the preferred ECG lead data in which such a QRS complex is detected is preferably divided into segments of a few seconds, for example 10 seconds. Segments may also be defined as a varied time span, which is proportional to the heart rate of the subject. Alternatively, this segmentation may be based on having a fixed number of heart beats included within any single segment.

Using a cross-correlation between the detected QRS complex waveform and the first segment data of each of the preferred leads, all QRS complexes are searched for and located within the first segment 1412. In order to discriminate against selection of noisy complexes such as PVC (Premature Ventricular Contraction), a cross-correlation value higher than 0.9, more preferably higher than 0.95, and even more preferably higher than 0.97, is required for the detection and selection of the other QRS complex waveforms within each segment. The threshold values for the cross-correlation are provided as an example only, and are not limiting.

The cross-correlation function in the neighborhood of each of the selected complexes is then fitted with a second order polynomial at the vicinity of each of the QRS complex temporal locations, using at least one more cross-correlation value point on each side of each local cross-correlation maximum point, preferably the nearest two cross-correlation value points on each side of each of the cross-correlation maxima. The second polynomial fit provides timing for each of the selected QRS complexes relative to the first detected QRS complex. The timing information provided by the fit is finer than the sampling timing points, and defines the relative alignment of the different QRS complexes within the segment, 1414.

Next, each aligned QRS complex is assigned with a time window starting before the QRS aligning point and ending after the QRS aligning point such that substantially the entire P-QRS-T waveform is contained within the window. Preferably, the window size, W, is in the range of 150-500 milliseconds, such as to include at least the QRS part of the ECG waveform.

Preferably, the window size is in the range of 350-450 milliseconds, whereby the zero point of the window is determined to be about 100 milliseconds before the alignment point. All QRS waveforms within a given segment which are defined by such a window are averaged together. The number of sampled points within a window may be given by $N_w=NW$, where N represents a sampling rate and W represents the window size. In a typical case the number $N_w=400$, in the case where the ECG signal is sampled at a rate N of 1000 Hz and W=400 milliseconds. The sampled data points within such a window may not coincide with each other among the different QRS complexes, since the alignment points of each of them, determined as described above, do not necessarily coincide with a single sampled point.

Continuing with stage 1414, in order to perform averaging of the waveforms, all QRS waveforms are transformed by local interpolation into the temporal points defined by the first detected QRS complex. Different interpolation methods may be used, as known in the art, preferably linear interpolation.

Averaging may be carried out according to the following modes:

a. simple averaging, where all data points (or interpolated data points) having the same time tag are averaged together;

b. weighted averaging, in which all data points (or interpolated data points) having the same time tag are weighted as known in the art using as weight factor, for example, the cross correlation value of the QRS complex of each segment;

c. averaging while removing outliers, in which all data points (or interpolated data points) having the same time tag, except the maximal value and minimal value data points within this group, or except the maximal m values and minimal n values, where m and n are pre-defined numbers, are averaged together, or alternatively computing the simple average of this group as in a., and then selecting only those points which are within a given distance from the average, for example within two standard deviations distance away from the average, and re-averaging the selected points;

d. performing singular value decomposition (SVD). SVD analysis may be carried out on some or all segments and it is then possible to select the waveform vector(s) which have the largest eigenvalue(s);

e. performing principal component analysis (PCA) analysis of partly or all segments.

The process of search, location and alignment of QRS complexes and QRS waveform definition and averaging continues with the following segments for each of the preferred ECG leads. The procedure branches back at stage 1416 for subsequent segments. The averaged QRS waveforms obtained in the first segment may now be used as a template for QRS complex detection. Other template building methods can be considered, including, but not limited to, use of the averaged QRS waveform of the first segment, or preferably the weighted-tail average of previous segments. This repetition may continue until a pre-defined number of segments is achieved, or until the entire recorded ECG signal is exhausted, at which case flow at decision box 1416 proceeds to stage 1418 and HF filtration of the average signals.

In stage 1418, the average value of all correlations of the averaged HF-QRS waveforms and their subsequent neighbors may be calculated per each of the preferred leads. The lead with the highest value for the average correlation may now be selected as the main lead. Other methods for selecting the main lead comprise preferring the lead with the maximum number of QRS complexes or preferring the lead with highest correlation of features in WB-QRS or any weighted combination of these methods. The skilled person will be aware of other suitable methods. It should be noted that the main lead may alternatively be pre-defined without going through the process detailed above.

As a further alternative it is possible to perform the above steps for all desired leads without selecting a main lead and then using the averaged and filtered QRS waveforms (the averaged HF-ECG waveforms).

The main lead thus obtained is in actual fact a list of QRS segments, each having an alignment temporal point relative to which the segment is defined, and each defining a QRS waveform. Preferably, the main lead is now used in stage 1422 for the definition and alignment of any subsequent recorded segments of the lead, including averaging, and HF filtering 1330, if the main lead is selected after an analysis of a pre-defined number of segments, which is the case in an indefinite recording of an ECG signal, such as in patient monitoring. If the main lead is selected after alignment and averaging of the entire recorded ECG data for this lead, further such analysis of the main lead is not required. Concurrently, the main lead is now used for the definition and alignment of all other leads that were recorded, or are being recorded further in the case of indefinite ECG recording, as the case may be.

The segments of these other leads, which may include any leads that were not selected as the main lead, are then averaged according to the procedure defined above, and in stage 1424 the averaged QRS waveform is filtered according to the procedure described above in order to provide averaged HF-QRS waveforms for these leads.

While defining a segment, the segment undergoes a cross-correlation with the preceding segment in order to discriminate against selection of a noisy segment, as described above. Such cross correlation may be carried out in stage 1420.

Once a segment is rejected according to the cross-correlation criteria, it is removed from the ECG recording, and its waveform is not used for further cross-correlation, waveform averaging and the like. Discrimination methods other than the cross-correlation of nearest neighbor waveforms could also be used, as known in the art.

Returning to FIG. 13, and in stage 1340, value indices are defined for the HF QRS waveforms, using the detected QRS positions. Each of the averaged HF QRS waveforms is assigned at least one value index. Such an index may be the RMS value of the waveform. Another value index may be obtained by using a low-pass filter on the squared amplitude values within each waveform, or alternatively using a low-pass filter on the absolute values of the amplitude within each waveform, and generating a waveform envelope, of which the peak value, and/or the area and/or the energy contained within the waveform may serve as a value index for the averaged HF QRS waveform.

Other indices may also be considered. The index itself may then be further averaged by using a function known as moving average, in which the value under consideration, together with a predefined number of preceding index values and another predefined number of subsequent index values are averaged together to provide an average index value for the averaged HF QRS waveform. The moving average thus forms a secondary index.

In general the additional noise reduction that is achieved by using a secondary index is necessary for patients undergoing the stress test since the patient's movements etc. introduce additional noise into the system. Patients being tested at rest may therefore not require the further noise reduction that is achieved by performing the moving average method. The moving average method may also not be required in cases in which value indices that are related to the variation of the HF-QRS signal rather than the amplitude, such as the STD value of the HF QRS waveforms, are formed.

In a final step of the method, the temporal behavior of the value indices (or their averages as discussed above) assigned to the averaged HF QRS waveforms of the different leads is analyzed 1350. This analysis can be performed at the end of a finite, pre-defined ECG acquisition, such as a stress test, or while monitoring the patient during any ECG acquisition, including but not limited to the duration of a stress test. In the monitoring case, an alert may be generated once the analysis of the temporal behavior of one or more of the value indices indicates a change in the patient's heart condition. Preferably, the analysis serves to determine the heart condition of the subject, for example detecting ischemic events or ischemic conditions. Preferably, such detection uses parameters as described below.

The Waveform Envelope Graph

In a preferred embodiment of the present invention, the user is provided with a waveform envelope graph. The waveform envelope graph is a two dimensional time-amplitude graph, which presents the ECG signal waveform indices described above, using the Y-axis to indicate time along each of the QRS positions, using the X-axis to indicate the running time, along the examination period, and using hue or color values, so as to indicate the changing amplitude of the signal or the signal's envelope in color. In this connection the reader is referred to U.S. Pat. No. 7,239,988 to Hasson et al, the contents of which are hereby incorporated by reference, which explains such a data representation.

Reference is now made to FIG. 15 which is an exemplary time-amplitude graph for presenting waveform envelope indices, according to a preferred embodiment of the present invention.

In FIG. 15, signals from two patients are presented, over a complete exercise test. Each vertical line in the figures represents the envelope of the HF signal of a single heartbeat, where the red color represents high amplitude and the blue color represents low amplitude. This presentation simplifies the detection of changes in the pattern and amplitude of the HF signal, allowing an easy separation of ischemic heart disease (IHD) subjects from healthy ones.

Using this exemplary time-amplitude graph, it is easy to see that the signal of the IHD subject 1510 undergoes a significant depression 1512 that eventually increases back to normal during the recovery period: the red color, representing a high amplitude of the signal envelope, disappears during the test 1512, denoting a decrease in HF amplitudes in the QRS positions. The HF amplitudes return to normal during recovery. The HF signal of the healthy subject 1520, on the other hand, does not show any significant change during exercise.

Example Parameters for Detecting Ischemic Events

During stress test, the heart rate (HR) increases from HR(rest) at rest, to HR(max) arrived at full effort. For each HR value during the test, an x % level may be defined according to the following equation:

$$HR = HR_{Rest} + x \cdot (HR_{Max} - HR_{Rest}).$$

The HF-ECG indices can be calculated for each HR level (x %) during the test. For example, $RMS_{70\%}$ is the RMS of the HF-ECG signal at an HR level which is 70% of the rate between rest and full effort. Alternatively, $SENV_{30\%}$ is the area under the envelope of the HF-ECG signal at an HR level of 30% between rest and maximal effort. Various parameters using these indices can be defined. For example:

$$p_1 = \frac{RMS_{100\%} + RMS_{90\%} + RMS_{80\%}}{RMS_{20\%} + RMS_{10\%} + RMS_{00\%}},$$

$$p_2 = \frac{RMS_{80-100\%}}{MAX\begin{pmatrix} RMS_{0-20\%}, RMS_{10-30\%}, RMS_{30-50\%}, \\ RMS_{50-70\%}, RMS_{70-90\%}, RMS_{90-100\%} \end{pmatrix}}$$

($RMS_{x-y\%}$ is the average RMS occurring between the x % and the y % of the HR), $$p_3 = \frac{SENV_{80-100\%}}{MAX\begin{pmatrix} SENV_{0-20\%}, SENV_{10-30\%}, SENV_{30-50\%}, \\ SENV_{50-70\%}, SENV_{70-90\%}, SENV_{90-100\%} \end{pmatrix}}$$

($SENV_{x-y\%}$ is the average SENV occurring between the x % and the y % of the HR). Using such parameters for the different leads, it is observed that parameters computed for healthy people are larger than those computed for patients having ischemic conditions, especially for the leads that are known in the art as V2, V3, V4 and L1. It is further observed that parameter $p_3$ has higher sensitivity (identifying sick people among the sick sub-population under a study) and higher specificity (identifying healthy people among the healthy sub-population under the same study) compared to the other two parameters $p_1$ and $p_2$.

Furthermore, one may select, for each subject under study, the two leads having the lowest parameter values (for a given parameter) out of the four leads mentioned above, and under such selection criteria improve the sensitivity and specificity of the identification of healthy and sick subjects.

Other parameters may be defined. These parameters may be based on the same or other value indices.

It is expected that during the life of this patent many relevant ECG devices and systems will be developed and the scope of the terms herein, particularly of the terms "Electrodes", "Leads", "Filter", and "Electrocardiogram", is intended to include all such new technologies a priori.

GLOSSARY OF TERMS USED

HF—high frequency—refers herein to the range above 100 Hz, preferably to the range of 100 Hz-500 Hz, and more preferably to the range of 150 Hz-250 Hz of the signal.

HF-QRS refers herein to the QRS part of the high frequency signal.

Wide Band ECG signal—ECG signal in is the full signal limited only by the system, for example the range of 0.05 Hz-500 Hz.

WB-QRS—Wide Band QRS—the QRS part of the wide band ECG signal.

Envelope of HF signal—Standard mathematical envelope function or any function of the HF signal yielding its outlining curvature.

Running average—a smoothing function replacing the value at each point by a new value calculated using its neighboring points. The simple option is averaging over a predefined window, but any smoothing method known in the art could be used, such as median, average without outliers, weighted average, a spline function or fitting to a predefined function.

Input unit includes a unit for receiving ECG signals from any kind of ECG source including leads placed externally or internal electrodes including implanted electrodes including implantable devices containing electrodes, that measure electromagnetic changes in the body due to heart activity.

The skilled person will appreciate that unless specifically mentioned otherwise the order of operations may be varied since for linear operations on a signal, the order should not change the results. In certain cases defined hereinabove, it is possible to use linear or close to linear operations such as band-pass filtering, and such a filtering operation may change place with any other operation even while using what is in fact a non-linear filter.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. Apparatus for QRS waveform quantifying, comprising:
an input unit, for receiving a plurality of high frequency (HF) range QRS complexes from at least one ECG lead;
a primary analyzer, associated with said input unit, for calculating a plurality of primary indices, each of said primary indices calculated from at least one of said plurality of high frequency (HF) range QRS complexes, wherein a first primary index is calculated from a first HF range QRS complex in a first time period and a second primary index is calculated from a second HF range QRS complex in a second time period, said first and second time periods being different and not coinciding; and a secondary analyzer, connected after said primary analyzer, for deriving a secondary index from said plurality of primary indices, thereby to provide a quantification of QRS complexes wherein said secondary index is a running average of said plurality of primary indices.

2. Apparatus according to claim 1, wherein said primary indices are a statistical function of said at least one of said plurality of high frequency (HF) range QRS complex.

3. Apparatus according to claim 1, wherein said primary indices are at least one of a group comprising:
   an RMS level of at least one HF QRS complex,
   a standard deviation within an HF QRS complex,
   a standard deviation over a plurality of HF QRS complexes,
   a function of an envelope of an HF QRS complex,
   a function of an envelope of a plurality of HF QRS complexes,
   an envelope maximum over an HF QRS complex,
   an envelope maximum over a plurality of HF QRS complexes,
   an envelope width of an HF QRS complex,
   an envelope width over a plurality of HF QRS complexes,
   a cross-correlation value of said HF QRS complex with a template waveform, and
   derivations of any one thereof.

4. Apparatus according to claim 1, wherein said secondary index is a function of:
   (a) a first primary index calculated by said primary analyzer from a first high frequency (HF) range QRS complex received at a first time period and
   (b) a second primary index calculated by said primary analyzer from a second high frequency (HF) range QRS complex received at a second time period.

5. The apparatus of claim 1, wherein said secondary analyzer is operable to use the secondary index to indicate at least one of the presence and severity of an ischemic event or an ischemic heart condition or ischemic heart disease.

6. Apparatus according to claim 1, wherein at least one of said primary analyzer and said secondary analyzer is configured to commence said calculating or said deriving respectively while said input unit continues to receive data, thereby providing an on-line quantification.

7. Apparatus for QRS waveform quantifying, comprising:
   an input unit, for receiving a plurality of high frequency (HF) range QRS complexes of ECG signals taken from a plurality of ECG leads of a given patient, as respective sets of amplitude values aligned over a time frame comprising time units such that there are a plurality of amplitude values for each time unit;
   a reduction unit, associated with said input unit, for removing at least one outward amplitude value for any given time unit from said sets, wherein said reduction unit is configured to remove any amplitude value lying outside a region defined by a statistical function of said amplitude values; and
   an analyzer, associated with said reduction unit, for calculating an overall index over said sets, using respective remaining amplitude values.

8. The apparatus of claim 7, wherein said complexes are derived from separate ECG signal leads.

9. The apparatus of claim 8, wherein said removing comprises removing at least one member of the group comprising a plurality of amplitude values, and all but a median amplitude value.

10. The apparatus of claim 7, wherein said complexes are derived from a single ECG signal lead.

11. The apparatus of claim 7, wherein said statistical function is a standard deviation.

12. Apparatus for QRS waveform quantifying, comprising:
   an input unit, for receiving a plurality of high frequency (HF) range QRS complexes obtained from a plurality of ECG leads at different locations on a subject;
   an alignment unit for aligning said complexes, so that complexes derived from different leads but at the same time are associated together, and
   a primary analyzer, associated with said alignment unit, for calculating a primary index to provide a single quantification of said associated complexes.

13. Apparatus for QRS waveform quantifying, comprising:
   an input unit, for receiving a plurality of high frequency (HF) range QRS complexes from at least one ECG signal taken from a plurality of ECG leads of a given patient, as respective sets of amplitude values aligned over a time frame comprising time units such that there are a plurality of amplitude values for each time unit; and
   a primary analyzer, associated with said input unit, for calculating a primary index for said plurality of high frequency (HF) ECG range QRS complexes, said calculating comprising using an envelope of said QRS complexes, wherein said primary analyzer is configured to remove any HF QRS complex lying outside a region defined by a statistical function of said complexes.

14. Apparatus according to claim 13, wherein said primary analyzer is configured to use a maximum of said envelope within a given time frame from which to derive said index.

15. Apparatus according to claim 13, wherein said analyzer is configured to use a width of said envelope within a given time frame, from which to derive said index.

16. Apparatus according to claim 13, wherein said analyzer is configured to use a statistical function of said envelope within a given time frame, from which to derive said index.

17. The apparatus of claim 13, wherein said high frequency range includes frequencies above 100 Hz.

18. The apparatus of claim 13, wherein said high frequencies range includes the 150 Hz-250 Hz range.

19. The apparatus of claim 13, wherein said index is presented to a user in a two time-dimensions and one amplitude dimension contour graph, where color indicates amplitude and both a horizontal and a vertical axis indicate time.

20. The apparatus of claim 13, wherein said analyzer is operable to use the index to indicate at least one of the presence and severity of ischemic events.

21. The apparatus of claim 20, wherein said index is a standard deviation and wherein said analyzer is configured to use an increase in said index to indicate the presence of ischemia.

22. The apparatus of claim 21, further configured to issue an alarm signal upon detection of an indication of ischemia.

* * * * *